United States Patent [19]

Kuesters et al.

[11] 4,287,367
[45] Sep. 1, 1981

[54] MANUFACTURE OF SYMMETRICAL OR UNSYMMETRICAL MONOACETALS OF AROMATIC 1,2-DIKETONES

[75] Inventors: Werner Kuesters; Lucien Thil, both of Ludwigshafen, Fed. Rep. of Germany

[73] Assignee: BASF Aktiengesellschaft, Fed. Rep. of Germany

[21] Appl. No.: 173,703

[22] Filed: Jul. 30, 1980

Related U.S. Application Data

[60] Continuation-in-part of Ser. No. 973,733, Dec. 27, 1978, abandoned, which is a continuation of Ser. No. 787,583, Apr. 14, 1977, abandoned, and a continuation-in-part of Ser. No. 935,623, Aug. 21, 1978, abandoned, which is a division of Ser. No. 787,569, Apr. 14, 1977, Pat. No. 4,144,156.

[30] Foreign Application Priority Data

Apr. 14, 1976 [DE] Fed. Rep. of Germany ....... 2616382
Apr. 14, 1976 [DE] Fed. Rep. of Germany ....... 2616408
Apr. 14, 1976 [DE] Fed. Rep. of Germany ....... 2616588

[51] Int. Cl.$^3$ ............................................. C07C 41/56
[52] U.S. Cl. ...................................... 568/43; 568/315
[58] Field of Search ................................. 568/43, 315

[56] References Cited

U.S. PATENT DOCUMENTS 3,715,293 2/1973 Sandner .......................... 204/159.14
4,190,602 2/1980 Brunisholz et al. .................. 568/315

FOREIGN PATENT DOCUMENTS 2232365 1/1974 Fed. Rep. of Germany .
2337813 2/1974 Fed. Rep. of Germany .

OTHER PUBLICATIONS

Kuhn, Chem. Ber., vol. 94, pp. 2258–2263, (1961).
Schmitz, Chem. Ber., vol. 91, pp. 410–414, (1958).

*Primary Examiner*—Natalie Trousof
*Assistant Examiner*—James H. Reamer
*Attorney, Agent, or Firm*—Keil & Witherspoon

[57] ABSTRACT

Monoacetals of aromatic 1,2-diketones are manufactured by reacting the corresponding 1,2-diketones, in an organic solvent, with an acid ester $(R^1)_nX$ as alkylating agent and an alcoholate $(R^2O)_m Me$, where $R^1$ and $R^2$ are identical or different hydrocarbon radicals of 1 to 12 carbon atoms, which may or may not be substituted, n and m are integers from 1 to 3, X is a monobasic, dibasic or tribasic acid radical and Me is a metal of main groups 1 to 3 of the periodic table of the elements. The resulting diketone monoacetals are particularly suitable for use as photoinitiators in photopolymerizable compositions.

28 Claims, No Drawings

MANUFACTURE OF SYMMETRICAL OR UNSYMMETRICAL MONOACETALS OF AROMATIC 1,2-DIKETONES

This application is a continuation-in-part of application Ser. No. 973,733, filed Dec. 27, 1978 now abandoned, which is a continuation of application Ser. No. 787,583, filed Apr. 14, 1977 now abandoned; and a continuation-in-part of application Ser. No. 935,623, filed Aug. 21, 1978 now abandoned, which is a divisional of application Ser. No. 787,569, filed Apr. 14, 1977 now U.S. Pat. No. 4,144,156.

The present invention relates to a new process for the manufacture of symmetrical or unsymmetrical monoacetals of aromatic 1,2-diketones from the corresponding 1,2-diketones.

The polymerization of unsaturated monomers, or of their mixtures with unsaturated polymers, by UV irradiation in the presence of photoinitiators has been disclosed. Though many photoinitiators are already known, their practical usefulness is restricted by some inherent disadvantages. For this reason, new compounds suitable for this application are of particular interest. The more recently discovered photoinitiators include compounds of the type of the benzilmonoacetals (cf. U.S. Pat. No. 3,715,293, German Laid-Open Applications DOS Nos. 2,232,365 and 2,337,813), which do not suffer from some of the disadvantages of earlier photoinitiators. The conventional process for the manufacture of compounds of this type is described by Kuhn and Trieschmann in Chemische Berichte 94 (1961), 2258 and in German Laid-Open Application DOS No. 2,337,813; according to this process, compounds of the benzil type are reacted with a dialkyl sulfite in the presence of an acid and an alcohol to give the corresponding monoacetals.

It would be desirable, however, to have an improved process for the manufacture of monoacetals of aromatic 1,2-diketones.

Chemische Berichte 91 (1958), pp. 410-414 discloses that certain active aldehydes can be reacted with dimethyl sulfate and dilute aqueous sodium hydroxide to yield 85 to 90% dimethyl acetals. However, this method for producing acetals is limited to specific aldehydes and 1,2-diketones cannot be converted to the corresponding monoacetals under these conditions.

It is an object of the invention to provide a further process for the manufacture of monoacetals of aromatic 1,2-diketones from the corresponding 1,2-diketones.

In particular, it is an object of the invention to provide an improved and simple process for the manufacture of symmetrical monoacetals of aromatic 1,2-diketones from the corresponding 1,2-diketones which gives the monoacetals in high yields under economically advantageous conditions.

It is another object of the invention to provide a new process for manufacturing unsymmetrical monoacetals of aromatic 1,2-diketones from the corresponding 1,2-diketones in high yields and purity.

Still further objects of the invention will be apparent from the following detailed description.

In accordance with this invention we have found that symmetrical or unsymmetrical monoacetals of aromatic 1,2-diketones of the formula (I)

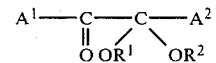

where $A^1$ and $A^2$ are identical or different aromatic radicals each of which has 6 to 12 carbon atoms and may or may not bear from one to four hydrocarbon radicals of 1 to 10 carbon atoms, alkoxy radicals of 1 to 10 carbon atoms, alkoxyalkyl radicals of 2 to 10 carbon atoms, alkylthio radicals of 1 to 6 carbon atoms and/or halogen as substituents; and $R^1$ and $R^2$ are identical or different hydrocarbon radicals of 1 to 12 carbon atoms in which the chain may or may not be interrupted by —O— or —S— or bear a halogen, can be manufactured particularly advantageously from corresponding aromatic 1,2-diketones of the formula (II)

by a method which comprises reacting the 1,2-diketones of the formula (II), in an organic solvent, with an acid ester $(R^1)_nX$ as alkylating agent and an alcoholate $(R^2O)_mMe$, where $R^1$ and $R^2$ have the above meanings, n and m are integers from 1 to 3, X is a monobasic, dibasic or tribasic acid radical and Me is a metal of the first 3 main groups (groups 1a, 2a and 3a) of the periodic table of the elements and especially a metal of atomic number from 11 to 20 from these groups of the periodic table of the elements.

Suitable aromatic 1,2-diketones of the formula (II) are especially those where $A^1$ and $A^2$ are a substituted benzene radical, suitable substituents being, above all, hydrocarbon radicals of 1 to 10 carbon atoms, e.g. alkyl or phenyl, alkoxyalkyl radicals of 2 to 10 carbon atoms, alkoxy radicals of 1 to 10 carbon atoms, alkylthio radicals of 1 to 6 carbon atoms and/or halogen.

Examples of particularly suitable aromatic 1,2-diketones which may be used for the process according to the invention are benzil and substituted benzils, e.g. 4,4'-dimethylbenzil, 4,4'-diisopropylbenzil, 4,4'-di-tert.-butylbenzil, 4,4'-diphenylbenzil, 2,2'-dimethyloxybenzil, 4,4'-dimethoxybenzil, 4-methylbenzil, 3-methoxybenzil, 2,2'-dimethylbenzil, 4-chloro-4'-phenylbenzil, 4,4'-dichlorobenzil, 3,3'-dibromobenzil, 2,4,2',4'-tetramethylbenzil, 2,4,6-trimethylbenzil and 2,4-dichloro-4'-methylbenzil. The manufacture of these benzil derivatives is described in the literature; for example, they may be manufactured by oxidizing the corresponding benzoins.

Alkylating agents suitable for the process of the invention have the above formula $(R^1)_nX$ and are esters of monobasic, dibasic or tribasic acids, especially of acids containing a sulfur, phosphorus or halogen atom. Examples are the esters of sulfuric acid, of sulfurous acid, of phosphoric acid and of phosphorous acid, the esters of hydrohalic acids, e.g. the chlorides, bromides and iodides, and the esters of aliphatic and aromatic sulfonic acids, such as the mesylates, tosylates, brosylates and benzene-sulfonates. The sulfates, halides and sulfonic acid esters are particularly suitable, and amongst these the sulfates are preferred. The ester radical $R^1$ is preferably a substituted or unsubstituted hydrocarbon radical of 1 to 12 carbon atoms, examples being, above all, the appropriate alkyl (especially of 1 to 6 carbon atoms), aralkyl (especially of 7 to 9 carbon atoms), alkenyl (especially of 3 to 5 carbon atoms) and aralkenyl (especially of 9 or 11 carbon atoms) radicals, and the groups Z—(CHR$^3$—CHR$^4$)p— or Z—(CHR$^3$)$_p$—, where p is an integer from 1 to 3, R$^3$ and R$^4$ are H or CH$_3$ and Z is halogen or OR$^5$, SR$^5$, OAr or SAr, where R$^5$ is alkyl of 1 to 4 carbon atoms or alkoxyalkyl of 2 to 5 carbon atoms and Ar is a six-membered aromatic radical.

Examples of alkylating agents which can be used for the process of the invention are dimethyl sulfate, diethyl sulfate, dihexyl sulfate, diallyl sulfate, dicrotyl sulfate, di-(β-phenylethyl) sulfate, di-(γ-phenylallyl) sulfate, di-(2-methoxyethyl) sulfate, di-(2-phenoxyethyl) sulfate, di-(methylthioethyl) sulfate and di-(2-phenylthioethyl) sulfate, benzyl bromide and allyl bromide.

Most of the suitable alkylating agents are known to those skilled in the art and are commercially available as such, sometimes being referred to as agents for basic or cold alkylation, or are simple to manufacture in accordance with processes disclosed in the literature.

Alcoholates used in the process of the invention have the above formula (R$^2$O)$_m$Me. As regards the nature of radical R$^2$, the meanings and data set forth above with respect to radical R$^1$ apply. Sodium and potassium alcoholates are preferred. If symmetrical monoacetals are to be prepared, alcoholates corresponding to the alkylating agents are used, i.e. in this case radicals R$^1$ and R$^2$ are identical. In the manufacture of symmetrical monoacetals, for example, a methylate, e.g. sodium methylate or potassium methylate, is used when using dimethyl sulfate as alkylating agent or, for example, sodium ethylate is used when using ethyl bromide as alkylating agent. In the process for the manufacture of unsymmetrical monoacetals of 1,2-diketones, alcoholates are used whose radicals R$^2$ do not correspond to the radical R$^1$ of the alkylating agent used, i.e. in this case the radicals R$^1$ and R$^2$ have the above meanings but are different from each other. Hence, when preparing unsymmetrical monoacetals, for example, an ethylate, e.g. sodium ethylate or potassium ethylate, is used when using dimethyl sulfate as alkylating agent, or, for example, sodium methylate is used when using allyl bromide as alkylating agent.

Examples of organic solvents or solvent mixtures which are suitable for the process of the invention are aromatic solvents, e.g. benzene, toluene, xylene or o-dichlorobenzene and aliphatic solvents, e.g. dioxane, tetrahydrofuran, glycol ethers, ethylene chloride, dimethylformamide and the like. Amongst these solvents, the polar aprotic solvents are particularly suitable. Dioxane and dimethylformamide are preferred. The amount of solvent should advantageously be such that after mixing all the reactants the reaction mixture can still be stirred easily. This is generally the case if the solvent accounts for at least about half the reaction mixture.

The reaction, according to the invention, if the 1,2-diketones with the alkylating agent and the alcoholate is in general carried out at from about −50° to about +150° C., preferably at from about −20° to about 100° C. The reaction time depends on the particular reactants, the temperature and the batch size. In general, however, the reaction is complete within a few hours and in some cases it is complete almost as soon as the reactants have been brought together.

Theoretically, 1/n mole of alkylating agent of the above formula (R$^1$)$_n$X is reacted with 1 mole of 1,2-diketone and 1/m mole of alcoholate of the above formula (R$^2$O)$_m$Me, with n and m in the fractions corresponding to the numbers n and m, respectively, in the formulae of the alkylating agent and alcoholate used, in order to produce symmetrical or unsymmetrical monoacetals of the aromatic 1,2-diketones. In general it is however preferred to use some of the reactants in excess in order to achieve complete conversion. Thus, from 1/n to 10/n mole or more, preferably from 1/n to 4/n mole, of alkylating agent, and from 1/m to 10/m mole or more, preferably from 1/m to 4/m mole, of alcoholate can be used per mole of 1,2-diketone.

In an advantageous embodiment of the process of the present invention, the process is carried out by introducing the alcoholate into a reaction mixture consisting of the aromatic 1,2-diketone, the alkylating agent and the solvent. The alcoholate can, in such cases, be added as the solid or as a slurry, for example in dimethylformamide, dioxane or tetrahydrofuran. A further possible way of adding the alcoholate is in the form of a very concentrated solution in the alcohol on which the alcoholate is based. An example is a solution of about 20% strength of sodium methylate in methanol. However, the process can also be carried out by adding the alkylating agent as the last component to the reaction mixture.

In a further embodiment of the process of the present invention, the reactants are brought together in optional sequence in a nonpolar solvent, e.g. toluene, preferably at room temperature, and the mixture is stirred. The reaction to give the 1,2-diketone monoacetal can be accelerated by gradually adding a polar solvent, e.g. dimethylformamide or dioxane.

After the reaction has ended (which can very easily be ascertained by, for example, thin layer chromatography), it is advisable to destroy any residual dimethyl sulfate by adding bases, e.g. ethanolamine or aqueous sodium hydroxide solution, with or without heating of the reaction mixture. During the process and isolation of the reaction products, it is necessary to ensure that the reaction mixture does not assume an acid pH since otherwise hydrolysis of the monoacetal to the corresponding 1,2-diketone may occur.

The reaction mixture can be worked up, and the reaction product isolated, by conventional processes, e.g. precipitation, extraction, distillation and the like. An example of a suitable procedure is simply to add water to the reaction solution, or run the reaction solution into water. Hereupon, the desired monoacetals of the 1,2-diketones frequently separate out as a crystalline precipitate or, in some cases, as oils. A precondition for this method is, however, that the solvent used for the reaction is water-miscible.

A particularly preferred possible method of working up the reaction solution is to remove the solvent from the reaction mixture, after addition of water, by azeotropic distillation. After this distillation the water-insoluble monoacetal separates out, especially on cooling, as a crystalline substance or as an oil, often in an analytically pure or virtually analytically pure form. This method offers the advantage that the solvent employed in the reaction can be substantially recovered.

Illustrative examples of symmetrical monoacetals of aromatic 1,2-diketones are benzil dimethyl monoketal, benzil diethyl monoketal, benzyl-dipropyl-monoketal, benzil diallyl monoketal, benzil di(β-phenylethyl) monoketal, benzil di(β-methoxyethyl) monoketal, benzil di(β-chlorethyl) monoketal, benzil (2-methylthioethyl) monoketal and similar compounds manufactured from the above mentioned substituted benzils. Examples of unsymmetrical monoketals of aromatic 1,2-diketones which can be obtained by the process described are benzil methyl-ethyl monoketal, benzil methylbenzyl monoketal, benzil methyl-crotyl monoketal, benzil methyl-allyl monoketal, 4,4'-dimethyl benzil ethyl-β-phenylethyl monoketal, 2,2'-dimethoxy benzil allyl-methylthioethyl monoketal, 4,4'-diphenyl benzil methyl-methoxyethyl monoketals and similar compounds manufactured from the aromatic 1,2-diketones, alkylating agents and alcoholates mentioned in this specification above.

Monoacetals obtained by the process of this invention are outstandingly suitable for use as photoinitiators in photopolymierzable compositions for coatings, optical information-fixing systems, printing plates and photoresists.

In the Examples which follow, parts and percentages are by weight. Parts by volume bear the same relation to parts as that of the liter to the kilogram.

EXAMPLE 1

78 parts of sodium methylate are added in portions in the course of 6 hours to a solution of 210 parts of benzil and 177 parts of dimethyl sulfate in 800 parts by volume of dioxane at room temperature, whilst stirring. A solution of 56 parts of sodium hydroxide in 1,000 parts by volume of water is then added to the reaction mixture and the batch is heated for about 1 hour under reflux. 1,100 parts by volume of solvent are then distilled off; virtually all the dioxane employed is recovered thereby.

The reaction mixture is then allowed to settle out at slightly above 70° C. The lower aqueous phase is separated off and discarded and the upper organic phase is stirred into 1,000 parts by volume of water. The precipitate is filtered off, washed with water and dried under reduced pressure at 40° C. Without employing any further purification, 246 parts (96% of theory) of analytically pure benzil dimethylketal of melting point 61°–62° C. are obtained.

EXAMPLE 2

6 parts of sodium methylate are added in portions in the course of 2 hours to a solution of 21 parts of benzil and 37 parts of p-toluenesulfonic acid methyl ester in 50 parts of dimethylformamide at room temperature, whilst stirring. The reaction mixture is then heated with 500 parts of water for 1 hour under reflux and subsequently cooled to room temperature, and the precipitate is filtered off and recrystallized from a mixture of isopropanol and water. 22 parts of benzil dimethylketal are obtained.

EXAMPLE 3

21.6 parts of sodium methylate are added in portions in the course of 3 hours to a solution of 52.5 parts of benzil and 68.4 parts of benzyl bromide in 400 parts by volume of dimethylformamide at room temperature, whilst stirring. The reaction mixture is then stirred for 30 minutes at room temperature, after which it is stirred into 2,000 parts by volume of water. The precipitate which separates out is filtered off, washed with water and dried. It is then suspended in 150 parts by volume of petroleum ether, filtered off, washed once with petroleum ether and dried. 62.0 parts of benzil methyl-benzyl-monoketal of melting point 83°–84° C. are obtained.

EXAMPLE 4

34 parts of sodium ethylate are added in portions, in the course of one hour, to a solution of 52.5 parts of benzil and 63 parts of dimethyl sulfate in 250 parts by volume of dioxane at room temperature, whilst stirring. After adding 300 parts by volume of water and 22 parts of solid sodium hydroxide, the reaction mixture is heated under reflux for 30 minutes, 350 parts by volume of dioxane/water azeotrope are then distilled from the reaction mixture, and the residue, after cooling to room temperature, is extracted with 150 parts by volume of chloroform. 2 parts of animal charcoal are added to the chloroform extract, the extract is boiled up and filtered and the solvent is evaporated off on a rotary evaporator. The oily, substantially colorless residue, the benzil methyl-ethyl-ketal, becomes crystalline after some time. Melting point 52°–54° C.

EXAMPLE 5

48 parts of sodium methylate are added in portions, in the course of 2.5 hours, to a solution of 105 parts of benzil and 121 parts of allyl bromide in 500 parts by volume of dimethylformamide at room temperature, whilst stirring. After adding 2,000 parts by volume of water, the reaction mixture is extracted with four times 100 parts by volume of chloroform and the combined chloroform extracts are then washed with three times 200 parts by volume of water. The chloroform phase is concentrated on a rotary evaporator and the residue is then distilled under reduced pressure. 115 parts of benzil methyl-allyl-ketal, boiling at 135°–136° C./0.3 mm Hg are obtained.

We claim:

1. A process for the manufacture of monoacetals of aromatic 1,2-diketones, of the formula (I)

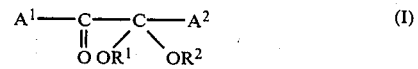

where $A^1$ and $A^2$ are identical or different aromatic radicals each of which has 6 to 12 carbon atoms and may or may not bear from one to four hydrocarbon readicals of 1 to 10 carbon atoms, alkoxy radicals of 1 to 10 carbon atoms, alkoxyalkyl radicals of 2 to 10 carbon atoms, alkylthio radicals of 1 to 6 carbon atoms and/or halogen as substituents, and $R^1$ and $R^2$ are identical or different hydrocarbon radicals 1 to 12 carbon atoms in which the chain may or may not be interrupted by —O— or —S— or bear a halogen, which comprises reacting aromatic 1,2-diketones of the formula (II)

in an organic solvent with an acid ester of the formula

as alkylating agent and an alcoholate

where $A^1$, $A^2$, $R^1$ and $R^2$ have the above meanings, n and m are integers from 1 to 3, X is a monobasic, dibasic or tribasic acid radical and Me is a metal of main groups 1 to 3 of the periodic table of the elements.

2. A process as set forth in claim 1, wherein the alcoholate is introduced into a reaction mixture consisting of the aromatic diketone, the alkylating agent and the solvent.

3. A process as set forth in claim 1, wherein an organic sulfate or a sulfonic acid ester is used as alkylating agent.

4. A process as set forth in claim 3 wherein the alkylating agent is selected from the group consisting of dimethyl sulfate, diethyl sulfate, dihexyl sulfate, diallyl sulfate, dicrotyl sulfate, di-($\beta$-phenylethyl) sulfate, di-($\gamma$-phenylallyl) sulfate, di-(2-methoxyethyl) sulfate, di-(2-phenoxyethyl) sulfate, di-(methylthioethyl) sulfate and di-(2-phenylthioethyl) sulfate.

5. A process as set forth in claim 1 wherein the alkylating agent is an ester of a hydrohalic acid.

6. A process as set forth in claim 5 wherein the alkylating agent is benzyl bromide or allyl bromide.

7. A process as set forth in claim 1, wherein the alcoholate is a sodium or potassium alcoholate.

8. A process as set forth in claim 1, wherein the organic solvent is dioxane or dimethylformamide.

9. A process as set forth in claim 1, wherein from $1/n$ to $10/n$ mole of the alkylating agent and from $1/m$ to $10/m$ mole of the alcoholate are used per mole of the aromatic 1,2-diketone.

10. A process as set forth in claim 1, wherein the reaction is carried out at a temperature from about $-50°$ C. to $+150°$ C.

11. A process for the manufacture of symmetrical monoacetals of aromatic 1,2-diketones, of the formula (I)

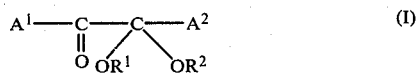

where $A^1$ and $A^2$ are identical or different aromatic radicals each of which has 6 to 12 carbon atoms and may or may not bear from one to four hydrocarbon radicals of 1 to 10 carbon atoms, alkoxy radicals of 1 to 10 carbon atoms, alkoxyalkyl radicals of 2 to 10 carbon atoms and/or halogen as substituents and $R^1$ and $R^2$ are identical hydrocarbon radicals of 1 to 12 carbon atoms in which the chain may or may not be interrupted by —O— or —S— or bear a halogen, which comprises reacting aromatic 1,2-diketones of the formula (II)

in an organic solvent with an acid ester of the formula

as alkylating agent and a corresponding alcoholate

where $A^1$, $A^2$, $R^1$ and $R^2$ have the above meanings, n and m are integers from 1 to 3, X is a monobasic, dibasic or tribasic acid radical and Me is a metal of main groups 1 to 3 of the periodic table of the elements.

12. A process as set forth in claim 11, wherein the alcoholate is introduced into a reaction mixture consisting of the aromatic diketone, the alkylating agent and the solvent.

13. A process as set forth in claim 11, wherein an organic sulfate or sulfonic acid ester is used as alkylating agent.

14. A process as set forth in claims 13 wherein the alkylating agent is selected from the group consisting of dimethyl sulfate, diethyl sulfate, dihexyl sulfate, diallyl sulfate, dicrotyl sulfate, di-($\beta$-phenylethyl) sulfate, di-(phenylallyl) sulfate, di-(2-methoxyethyl) sulfate, di-(2-phenoxyethyl) sulfate, di-(methylthioethyl) sulfate and di-(2-phenylthioethyl) sulfate.

15. A process as set forth in claim 11, wherein the alcoholate is a sodium or potassium alcoholate.

16. A process as set forth in claim 11, wherein the organic solvent is dioxane.

17. A process as set forth in claim 11, wherein the organic solvent is dimethylformamide.

18. A process as set forth in claim 11, wherein from $1/n$ to $10/n$ mole of the alkylating agent and from $1/m$ to $10/m$ mole of the alcoholate are used per mole of the aromatic 1,2-diketone.

19. A process as set forth in claim 11, wherein the reaction is carried out at a temperature from about $-50°$ C. to $+150°$ C.

20. A process for the manufacture of unsymmetric monoketals of aromatic 1,2-diketones having the formula (I)

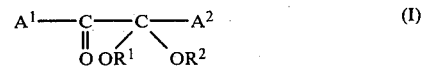

where $A^1$ and $A^2$ are identical or different aromatic radicals each of which having from 6 to 12 carbon atoms which may or may not bear from one to four substituents selected from the group consisting of hydrocarbon radicals having 1 to 10 carbon atoms, alkoxy radicals having 1 to 10 carbon atoms, alkoxyalkyl radicals having 2 to 10 carbon atoms, alkylthio radicals having 1 to 6 carbon atoms and halogen; and $R^1$ and $R^2$ are different hydrocarbon radicals 1 to 12 carbon atoms in which the chain may or may not be interrupted by —O— or —S— or bear a halogen, which comprises reacting aromatic 1,2-diketones of the formula (II)

in an organic solvent with an acid ester $(R^1)_nX$ as alkylating agent and an alcoholate $(R^2O)_m$Me, where $A^1$, $A^2$, $R^1$ and $R^2$ have the above meanings, n and m are integers from 1 to 3, X is a monobasic, dibasic or tribasic acid radical and Me is a metal of main groups 1 to 3 of the periodic table of the elements.

21. A process as set forth in claim 20, wherein the alcoholate is introduced into a reaction mixture consisting of the aromatic diketone, the alkylating agent and the solvent.

22. A process as set forth in claim 20, wherein an organic sulfate, or sulfonic acid ester or ester of a hydrohalic acid is used as alkylating agent.

23. A process as set forth in claim 22, wherein the alkylating agent is selected from the group consisting of dimethyl sulfate, diethyl sulfate, dihexyl sulfate, diallyl sulfate, dicrotyl sulfate, di-($\beta$-phenylethyl) sulfate, di-(phenylallyl) sulfate, di-(2-methoxyethyl) sulfate, di-(2- phenoxyethyl) sulfate, di-(methylthioethyl) sulfate and di-(2-phenylthioethyl) sulfate.

24. A process as set forth in claim 22, wherein the alkylating agent is benzyl bromide or allyl bromide.

25. A process as set forth in claim 20, wherein the alcoholate is a sodium or potassium alcoholate.

26. A process as set forth in claim 20, wherein the organic solvent is dioxane or dimethylformamide.

27. A process as set forth in claim 20, wherein from 1/n to 10/n mole of the alkylating agent and from 1/m to 10/m mole of the alcoholate are used per mole of the aromatic 1,2-diketone.

28. A process as set forth in claim 20, wherein the reaction is carried out at a temperature from about $-50°$ C. to $+150°$ C.

* * * * *